United States Patent [19]

Michaels

[11] 4,183,952

[45] Jan. 15, 1980

[54] ANTIMICROBIAL COMPOSITIONS

[76] Inventor: Edwin B. Michaels, Gregory Ct., East Norwalk, Conn. 06855

[21] Appl. No.: 641,729

[22] Filed: Dec. 18, 1975

[51] Int. Cl.$^2$ ..................................... A61K 31/205
[52] U.S. Cl. ..................... 424/316; 424/65; 424/320; 424/325; 252/106
[58] Field of Search ............... 424/316, 320, 325, 329, 424/65; 252/106

[56] References Cited

U.S. PATENT DOCUMENTS

| | | | |
|---|---|---|---|
| 3,280,179 | 10/1966 | Ernst | 424/329 |
| 3,484,523 | 12/1969 | Findlan et al. | 424/248 |

OTHER PUBLICATIONS

Kirk-Othmer Encyc. of Chem. Tech., vol. 19 (1969), pp. 555–557.

Primary Examiner—V. D. Turner

[57] ABSTRACT

There is provided an antimicrobial composition of low toxicity having enhanced gram positive and gram negative activity and consists essentially of:

(a) an alkyl-N-sulfobetaine (0.1 part–40.0 parts, by weight), (b) an alkyl-N,N-dimethylamine oxide, an alkyl-N,N-dihydroxyethylamine oxide, or an acylamido t-amine oxide (0.1 part–40.0 parts, by weight), and (c) a protonating agent, such as hydrochloric acid, acetic acid, in an amount sufficient to adjust the pH of the overall composition to about 5.5 or below.

The composition exhibits skin degerming, cleansing, and deodorizing properties and, particularly, its use exhibits long term inhibition of body odor.

8 Claims, No Drawings

ANTIMICROBIAL COMPOSITIONS

The present invention relates to antimicrobial compositions of enhanced efficacy and safety. More particularly, the invention relates to antimicrobial compositions having low toxicity and broad spectrum antimicrobial activity comprising certain amphoteric surfactants which per se have limited antimicrobial use. Still more particularly, the invention is concerned with antimicrobial compositions of enhanced gram positive and gram negative activity consisting essentially of in admixture:

(a) an alkyl-N-sulfobetaine (0.1–40.0 parts, by weight), (b) an alkyl-N,N-dimethylamine oxide, an alkyl-N,N-dihydroxyethylamine oxide, or an acylamido t-amine oxide (0.1–40.0 parts, by weight), and (c) a protonating agent, such as hydrochloric acid, acetic acid or citric acid in an amount sufficient to adjust the pH of the overall composition to about 5.5, or below.

The compositions of the present invention exhibit sustained periods of antimicrobial activity, particularly in the control of body odor.

As is known, an outstanding method for the control of body odor is to thoroughly wash the body with soap, but so prolific are the microbial flora of the skin that distinctive malodors tend to return within several hours after washing. To provide longer periods of protection, there have been developed compositions which either contain (a) astringents, such as aluminum chlorohydrate, that inhibit apocrine and eccrine gland secretions or contain (b) antimicrobial agents, such as hexachlorophene and trichlorocarbanilamide. Unfortunately, astringent compositions have limited value, since they have little or no control of microbial decomposition of debris and uncontrolled secretions and where there is control of secretions, such use suffers from severe shortened periods so as to obtain effective control. Nonetheless, the latter antimicrobial compositions have enjoyed widespread use. Nonetheless, there have been recent investigations into topical and systemic toxicity of the hereinabove named germicides used to control body odor. These investigations have led to severe restrictions, for instance, on the utilization of hexachlorophene and the recognition of the dangers of other germicides. Further, the use of astringents have only limited utility usually due to its harsh action on skin, particularly, on those who have sensitive skin. If a safe and effective antimicrobial composition of low toxicity could be provided which would inhibit the development of body odor for relatively long periods of time, eg., at least twenty-four (24) hours, or longer, such a composition would satisfy a real need in the art.

It is a principal object of the invention to provide an antimicrobial composition of enhanced efficacy and safety which possesses broad spectrum activity in combating body odor and topical infections. It is a further object of the invention to provide an antimicrobial composition comprising at least an alkyl-N-sulfobetaine surfactant and an alkyl-N,N-dimethylamine oxide, and acylamido t-amine oxide, or an alkyl-N,N-dihydroxyethylamine oxide adjusted to a pH of 5.5, or below, so as to control gram positive bacteria, gram negative bacteria, fungi, and yeast, when topically applied. Other objects and advantages will become apparent from a consideration of the ensuing description.

According to the invention, there are provided antimicrobial compositions comprising a mixture of (a) an alkyl-N-sulfobetaine and (b) an alkyl-N,N-dimethylamine oxide, an acylamido t amine oxide, or an alkyl-N,N-dihydroxyethylamine oxide. The components are admixed at a temperature ranging from about 25° C. to 80° C. in a substantially aqueous or non-aqueous environment and adjusted to a pH of 5.5, or below, to provide a substantially uniform homogeneous composition having both enhanced broad spectrum activity and low toxicity.

In general, the alkyl-N-sulfobetaine surfactant employed as a zwitterion component of the composition can be written as:

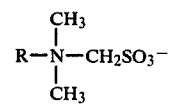

where R is a higher alkyl having from 10 to 18 carbon atoms. Illustrative of such alkyl-N-sulfobetaine are coco-N-sulfobetaine, cetyl-N-sulfobetaine, stearyl-N-sulfobetaine, isostearyl-N-sulfobetaine, oleyl-N-sulfobetaine, or mixtures of the same.

The (1) alkyl-N,N-dimethylamine oxide, (2) dihydroxyethylamine oxide, or (3) acylamido t-amine oxide component of the aforementioned mixture, respectively has the structure:

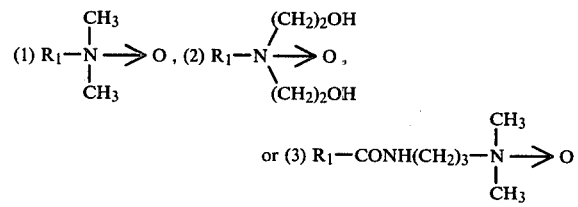

where $R_1$ is a higher alkyl from 10 to 18 carbon atoms, as for instance, radicals such as decyl, undecyl, lauryl, tridecyl, myristyl, cetyl, stearyl, isostearyl, oleyl or mixtures of the same. Exemplary of the latter amine oxides are decyl-N,N-dimethylamine oxide, lauryl-N,N-dimethylamine oxide, stearyl-N,N-dimethylamine oxide, oleyl-N,N-dimethylamine oxide, cocoamido-trimethylene-N,N-dimethylamine oxide, stearylamido-trimethylene-N,N-dimethylamine oxide, decyl-N,N-dihydroxyethylamine oxide, lauryl-N,N-dihydroxyethylamine oxide, coco-N,N-dihydroxyethylamine oxide, stearyl-N,N-dihydroxyethylamine oxide, oleyl-N,N-dihydroxyethylamine oxide, and mixtures of the same.

In general, the protonating agent necessary to supply the required pH to the overall composition is, for instance, any inert organic or inorganic acid, such as hydrochloric acid, phosphoric acid, sulfuric acid, citric acid, acetic acid, nicotinic acid, and the like. A good operating pH range for the overall composition is 4.0 to 5.5 and, preferably, from about 4.7 to 5.2. The pH of an aqueous solution comprising the above enumerated components of the invention is determined by employing 0.5%, by weight, of active components at a glass electrode to precisely define the acidity of the composition.

In practice, each of the components of the overall composition ranges widely from 0.1 part to 40.0 parts and the balance an inert solvent, such as water or a lower monohydric aliphatic alcohol for a total of at least 100 parts. Where water is employed, small amounts of a lower alkyl alcohol may also be added thereto to provide ease in formulation. The pH of the total composition is then adjusted to the requisite pH by adding a suitable inorganic or organic acid thereto. The composition can be employed as a solution or as a spray, such as an aerosol spray utilizing commercially available "Freon" fluorocarbon or equivalent propellant.

Advantageously, the compositions of the present invention possess an extremely low toxicity exhibiting as an $LD_{50}$ in Swiss-Webster mice greater than four (4) grams per kilogram by intraperitoneal or oral administration. Further, there are observed a lack of primary irritation to the skin and less eye irritation as compared with ordinary soap.

It has been found that the aforementioned compositions can be used in a plurality of ways. For instance, when applied to pyogenic wound infections, rapid healing is promoted. When used as an ear douche, the compositions can relieve ear infections and eliminate those mild microbial infections known as dandruff, crotch itch, athletes foot and the like. As stated above and as shown in the examples hereinbelow set forth, when the compositions of the invention are employed as a general personal body wash, body odor in the axillary and anal or genital areas in particular will be inhibited for periods in excess of twenty-four (24) hours and usually, will exhibit odor inhibition from seventy-two (72) to ninety-six (96) hours.

In order to facilitate a further understanding of the invention, the following examples are presented primarily for purposes of illustrating certain more specific details thereof. The invention is not to be deemed as limited thereby except as defined in the claims. Unless otherwise noted, all parts and percentages are by weight.

EXAMPLE 1

In this example, several compositions are prepared and used as a body wash. Twelve panels each consisting of five men and five women as subjects are selected and supplied with samples of the compositions herein defined in Table I below. After twenty-four (24) hours have elapsed since the panel members' last washing, each is instructed to wash, noting particularly the axillary odor before and after washing. The panel members are then examined during the next twenty-four (24) hours and longer for the time span when typical body odors develop. These times are then noted and recorded in Table I below.

TABLE I

| Panel No. | Composition | Average Elapsed Time Body Odor is Detected (hours) |
|---|---|---|
| 1. | Cocoamido-N,N-dimethylamine oxide-12% actives in distilled water (pH=7) | 8 |
| 2. | Cocoamido-N,N-dimethylamine oxide-12% actives in distilled water - pH adjusted to 5.4 with citric acid. | 10 |
| 3. | Coco-N-sulfobetaine-12% actives in distilled water - pH measured at 6.8 | 12 |
| 4. | Coco-N-sulfobetaine-12% actives in distilled water - pH adjustd to 5.4 with citric acid | 12 |
| 5. | Coco-N-sulfobetaine-6% in distilled water, plus coco-N,N-dimethylamine oxide-6% in distilled water at pH=6.4 | 12 |
| 6. | Coco-N-sulfobetain-6% in distilled water, plus cocoamido-N,N-dimethylamine oxide-6% in distilled water citric acid-0.55% in distilled water at a pH=5. with citric acid | 48–96 |
| 7. | Cetyl-N-sulfobetain-4% in distilled water, plus myristyl/palmitic-N,N-dimethylamine oxide-6% in distilled water adjusted to pH-5 with acetic acid | 48–72 |
| 8. | Cetyl N-sulfobetain-6% in distilled water, plus Oleyl-N,N-dimethylamine oxide-6% in distilled water, adjusted to pH=5.5 with citric acid | 48–60 |
| 9. | 70/30 Myristyl/palmitic-N,N-dimethylamine oxide-12% in distilled water-pH adjusted to 5.5 with citric acid | 12 |
| 10. | Decyl-N,N-dimethylamine oxide-12% actives in distilled water-pH adjusted to 5.2 with acetic acid | 8 |
| 11. | 70/30 Myristyl/palmitic-N,N-dimethylamine oxide-6%+lauryl-N,N-dimethylamine oxide-6% in distilled water, adjusted to a pH=5.2 with citric acid | 10 |
| 12. | 70/30 Myristyl/palmitic-N,N-dimethylamine oxide-6%+coco-N-sulfobetaine-6% in distilled water, adjusted to a pH=5.1 with citric acid | 36–48 |

From the above table, it can be clearly seen that the compositions of the present invention at the adjusted pH range cause a marked improvement in body odor inhibition.

EXAMPLE 2

The relation between antimicrobial activity and control of body odor is determined by subjecting each of the panel members of Example 1 to additional washing tests employing the compositions of Example 1. There are obtained the density of microbes in the axillary area of each panelist by using a Rodac plate comprising Tryptose soy agar with Tween ®80 and lecithin to neutralize any residual germicide. The panelist presses the plate for 30 seconds to the axillary area of the armpit. The plates are then incubated at 37° C. for 24 hours and the number of colonies are counted. The density in the colonies per square inch is next calculated. The data obtained are noted in the table below and are the average values of the subjects treated.

TABLE II

| Composition of Example 1 | 0 Hours after washing | 12 Hours after washing | 24 Hours after washing | 48 Hours after washing |
| --- | --- | --- | --- | --- |
| 1 | 1000 | 2300 | TNC* | TNC |
| 2 | 1200 | 2500 | TNC | TNC |
| 3 | 1400 | 2450 | TNC | TNC |
| 4 | 1150 | 2650 | TNC | TNC |
| 5 | 1350 | 2700 | TNC | TNC |
| 6 | 450 | 800 | 1400 | 2200 |
| 7 | 380 | 650 | 1000 | 1400 |

*TNC means too numerous to count - the density is greater than 30000 colonies per square inch.

EXAMPLE 3

There are admixed at 40° C. stearyl-N-sulfobetaine (6.25 gm.), coco-N, N-dimethylamine oxide (13 gm.) citric acid (4.5 gm.) and 125 gm. of distilled water. The pH of the mixture when diluted to 0.5% actives is equal to 5.0.

The mixture is tested as a body shampoo and after 60 hours subsequent to washing, the panel reported no evidence of body odor in the axillary areas.

EXAMPLE 4

A mixture of stearyl-N-sulfobetaine (6.5 gms.), coco-N,N-dimethylamine oxide (13 gms.), acetic acid (4.5 gms.), and 66 gms. of water, formed at 50° C. and having a pH on dilution is equal to 5.1, is employed as a body wash as in Example 3 above. Body odor is absent after seventy-two (72) hours.

Substituting hydrochloric acid for acetic acid in the above mixture, similar results are noted.

EXAMPLE 5

There are admixed cetyl-N-sulfobetaine (2.5 gms.), myristyl-N,N-dimethylamine oxide (5.5 gms.), citric acid (2.0 gms.) and 87 gms. of water. The mixture is heated to 60° C. and the pH determined on dilution is 5.5.

As in Example 4 above, the mixture is used as a body wash to determine axillary and pubic body odors. After 72 hours subsequent to washing, no body odor is detected. Moreover, panel members with dandruff report complete control of dandruff after two days' use when washing once each day with the above composition.

EXAMPLE 6

A mixture of lauryl-N-sulfobetaine (5.2 gms.), 70/30 myristyl/palmitic-N,N-dimethylamine oxide mixture (5.5 gms.) citric acid (0.7 gms.) and water (108 gms.) is heated to 35° C. The pH of the diluted solution is 5.4 and is used as a body wash. No body odor is detected for seventy-two (72) hours after washing.

EXAMPLE 7

There are added at 30° C. 6.2 gms. of coco-N-sulfobetaine, 6.2 gms. of 70/30 myristyl/palmitic-N,N-dihydroxyethylamine oxide, 5. gms. of isopropanol, 0.7 gms. of citric acid, and 92 gms. of water. Upon dilution, the pH measured equals 5.5.

The mixture is used as a body shampoo and controls body odor for 48 hours after washing in all panel members.

EXAMPLE 8

There are admixed at 75° C., 10 gms. of cetyl-N-sulfobetaine, 10 gms. of coco-N-betaine, 42 gms. of 70/30 myristyl/palmitic-N,N-dimethylamine oxide, 15 gms. of isopropanol, 9 gms. of citric acid, and 550 gms. of water. There is obtained a solution having a pH=5.0 on dilution and the preparation when used as a body wash controls odor for more than 72 hours after washing.

EXAMPLE 9

This example illustrates the formulation of a solid composition comprising of 32 gms. of stearyl-N-sulfobetaine, 32 gms. of myristyl/palmitic-N,N-dimethylamine oxide, 32 gms. of 2-stearyl-1-(ethyl-B-oxypropionic acid) imidazoline, 20 gms. of isopropanol, 40 gms. of water and 6.3 gms. of citric acid. The mixture is vigorously stirred and heated to a temperature of 80° C. Resultant composition is then dried by evaporation and cooled. There is recovered 110 gms. of a waxy solid product having a pH equal to 5.0 at a 0.5% aqueous concentration.

The solid composition is employed as solid detergent for washing and controls body odor for 48 hours after washing.

EXAMPLE 10

In this example there is prepared a spray composition. There are admixed 0.1 gm. cetyl-N-sulfobetaine, 0.1 gm. coco-N,N-dimethylamine oxide, 10 gms. isopropanol, and 0.02 gm. of citric acid. The mixture is heated to 40° C., cooled, and admixed with 100 gms. of liquified butane in a suitable container.

Resultant composition is sprayed under the armpits of several panelists. Each reports underarm odor control for at least 48 hours after use.

EXAMPLE 11

There are added to a suitable mixing vessel with stirring, 8 gms. of coco-N-betaine, 8 gms. of stearyl-N-sulfobetaine, 16 gms. of 70/30 myristyl/palmitic-N,N-dimethylamine oxide, 3.3 gms. of citric acid and q.s. to 250 gms. of water. Resultant mixture is stirred vigorously and heated to 60° C. for fifteen minutes.

Upon cooling, the pH of the mixture is found to possess a pH equal to 4.7 on dilution.

Resultant composition is employed as a body wash following the procedure of Example 2 above. After 12 hours, it is found by each of five panelists that no body odor is detected and a bacterial count of 190 colonies per square inch is obtained. After 36 hours, no body odor is reported and the bacterial count rose to 600 colonies per square inch. The controls, however, in 36 hours all reported detectable body odor and bacteria colonies too numerous to count, when each of the controls constituting five panelists employs a modified composition of this example in which citric acid is omitted. The pH of the latter composition, on dilution, is 7.4.

Advantageously, the compositions of the present invention, and particularly, as exemplified in each of the above examples, are employed in successfully treating pyogenic infections. The treatment consists of cleaning the wound by washing the same with the composition of the invention and then covering the wound for about 4 to 5 hours. In all cases, irritation and inflammation cease within the four to five hour period, and most wounds exhibit satisfactory healing within two to three days thereafter.

I claim:

1. A broad spectrum antimicrobial composition having low toxicity which consists essentially of:
   (a) 0.1 to 40 parts, by weight, of a higher alkyl-N-betaine said betaine having the structure:

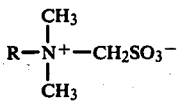

where R is a higher alkyl of from 10 to 18 carbon atoms,
   (b) 0.1 to 40 parts, by weight, of a higher alkyl-N,N-dimethylamine oxide, a higher alkyl-N,N-dihydroxyethylamine oxide, or an acylamido t-amine oxide having the respective structure:

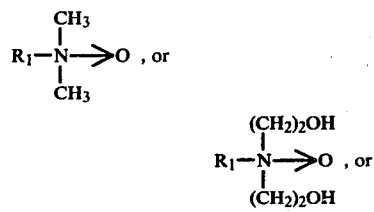

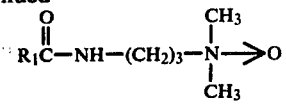

where $R_1$ is a higher alkyl of from 10 to 18 carbon atoms, or mixtures of the same, and
   (c) a protonating agent, sufficient to adjust the pH of said composition from 4 to 5.5.

2. The composition according to claim 1 wherein the alkyl-N-betaine is coco-N-sulfobetaine.

3. The composition according to claim 1 wherein the alkyl-N-betaine is stearyl-N-sulfobetaine.

4. The composition according to claim 1 wherein the higher alkylamine oxide is coco-N,N-dimethylamine oxide.

5. The composition according to claim 1 wherein the higher alkylamine oxide is stearyl-N,N-dihydroxyethylamine oxide.

6. The composition according to claim 1 wherein the protonating reagent is citric acid.

7. The broad spectrum, antimicrobial composition according to claim 1 wherein the protonating reagent is acetic acid.

8. The composition according to claim 1 wherein the composition is dissolved in an aqueous medium and wherein the pH of the aqueous mixture is adjusted to and maintained at from 4.7 to 5.2.

* * * * *